(12) United States Patent
Chu et al.

(10) Patent No.: US 8,217,044 B2
(45) Date of Patent: *Jul. 10, 2012

(54) SPIROINDOLINONE PYRROLIDINES

(75) Inventors: Xin-Jie Chu, Livingston, NJ (US); Qingjie Ding, Bridgewater, NJ (US); Nan Jiang, Pine Brook, NJ (US); Jing Zhang, Parsippany, NJ (US); Zhuming Zhang, Hillsborough, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/072,872

(22) Filed: Mar. 28, 2011

(65) Prior Publication Data

US 2011/0269809 A1 Nov. 3, 2011

Related U.S. Application Data

(60) Provisional application No. 61/328,711, filed on Apr. 28, 2010.

(51) Int. Cl.
| | |
|---|---|
| *A61K 31/4025* | (2006.01) |
| *A61K 31/407* | (2006.01) |
| *A61K 31/4155* | (2006.01) |
| *A61K 31/4178* | (2006.01) |
| *A61K 31/427* | (2006.01) |
| *A61K 31/4439* | (2006.01) |
| *A61K 31/497* | (2006.01) |
| *A61K 31/501* | (2006.01) |
| *A61K 31/506* | (2006.01) |
| *C07D 209/54* | (2006.01) |
| *C07D 401/14* | (2006.01) |
| *C07D 403/14* | (2006.01) |
| *C07D 405/14* | (2006.01) |
| *C07D 417/14* | (2006.01) |

(52) U.S. Cl. ............... 514/252.06; 514/255.05; 514/406; 514/338; 514/256; 514/365; 514/397; 514/375; 548/410; 548/181; 548/217; 548/364.4; 548/305.1; 544/238; 544/333; 544/373; 546/277.7

(58) Field of Classification Search .................. None
See application file for complete search history.

(56) References Cited

U.S. PATENT DOCUMENTS

| | | |
|---|---|---|
| 2,759,935 A | 8/1956 | Speeter |
| 3,441,570 A | 4/1969 | Meyer |
| 3,686,210 A | 8/1972 | Bell |
| 4,020,179 A | 4/1977 | Irvine |
| 6,511,974 B1 | 1/2003 | Dusza et al. |
| 6,774,132 B1 | 8/2004 | Claesson et al. |
| 7,495,007 B2 | 2/2009 | Chen et al. |
| 7,553,833 B2 | 6/2009 | Liu et al. |
| 7,638,548 B2 | 12/2009 | Liu et al. |
| 2008/0009486 A1 | 1/2008 | Chen et al. |
| 2008/0114013 A1 | 5/2008 | Liu et al. |

FOREIGN PATENT DOCUMENTS

| | | |
|---|---|---|
| EP | 0288847 | 4/1988 |
| EP | 0947511 | 10/1999 |
| JP | 55 129284 | 6/1980 |
| JP | 2000191661 | 7/2000 |
| WO | 97/15556 | 5/1997 |
| WO | 98/02432 | 1/1998 |
| WO | 98/54167 | 12/1998 |
| WO | 00/15657 | 3/2000 |
| WO | 00/71129 | 11/2000 |
| WO | 01/05790 | 1/2001 |
| WO | 03/008407 | 1/2003 |
| WO | 03/078394 | 9/2003 |
| WO | 2006/080574 | 8/2006 |
| WO | 2006091646 | 8/2006 |
| WO | 2006/136606 | 12/2006 |
| WO | 2007104664 | 9/2007 |
| WO | 2007104714 | 9/2007 |
| WO | 2008036168 | 3/2008 |
| WO | 2008/055812 | 5/2008 |
| WO | 2008080822 | 7/2008 |
| WO | 2008005268 | 10/2008 |
| WO | 2009080488 | 7/2009 |

OTHER PUBLICATIONS

U.S. Appl. No. 12/939,237, filed Nov. 2010, Bartkovitz, D.*
Simplicio, Ana, Molecule, 2008, 519-547.
Sairim, Carbohydrate Research 338__2003__303-306.
Sun, Cancer Biology & Therapy, (2008), 7 (6), 845-852.

(Continued)

*Primary Examiner* — Yong Chu
*Assistant Examiner* — Michael Barker
(74) *Attorney, Agent, or Firm* — George W. Johnston; Patricia S. Rocha-Tramaloni

(57) ABSTRACT

There are provided compounds of the formula

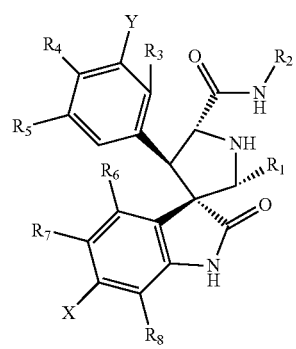

I wherein X, Y and $R_1$ to $R_8$ are as described herein and the enantiomers and pharmaceutically acceptable salts and esters thereof which compounds have anticancer activity.

5 Claims, No Drawings

OTHER PUBLICATIONS

Ansel et al., Pharmaceutical Dosage Forms and Drug Delivery Systems (6th Ed. 1995) at pp. 196.
Ansel et al., Pharmaceutical Dosage Forms and Drug Delivery Systems (6th Ed. 1995) at p. 456-457.
Kraynack, E. A.; Dalgard, J. E.; Gaeta, F. C. A. Tetrahedron Letters, 1998, 39, 7679-7682.
P. Erway, et al., J. Med. Chem 2002, 45, 1487-1499.
Elliott, I. W.; Rivers, P. J. Org. Chem 1964, 29, 2438-2440.
Andreani, A.; et al., Eur. J. Med. Chem. 1990, 25, 187-190.
Christopher Hulme, et al., Bioorganic & Medicinal Chemistry Letters, vol. 8, pp. 175-178 (1998), XP002405133.
F.D. Dopp, et al., J. Heterocyclic Chem., vol. 17, No. 9, pp. 1329-1330 (1980) XP002405134.
Gordon N. Walker, et al., J. Med. Chem., vol. 8, pp. 626-637 (1965) XP002405135.
Stanislav Kafka, et al., J. Org Chem., vol. 66, pp. 6394-6399 (2001) XP002405136.
Amarnath Natarajan, et al., J. Med. Chem., vol. 47, pp. 1882-1885 (2004) XP002405137.
James C. Powers, J. Org. Chem., vol. 30, pp. 2534-2540 (1965), XP002405138.
Sengodagounder Muthusamy, et al., Synlett, vol. 2002, No. 11, pp. 1783-1786 (2002) XP002405139.
Ward C. Sumpter, J. Am. Chem Soc., vol. 64, pp. 2917-291 8(1932), XP002405141.
H.E. Zaugg, et al., J. Am. Chem. Soc., vol. 84, pp. 4574-4578 (1962) XP002418406.
Steven P. Govek, et al., J. Am. Chem. Soc., vol. 123, pp. 9468-9469 (2001), XP002418407.
Rita Kapiller-Dezofi, et al., New J. Chem., vol. 28, pp. 1214-1220 (2004), XP002418408.
David W. Robertson, et al., J. Med. Chem., vol. 29, pp. 1832-1840 (1986), XP002418409.
Kazuo Takayama, et al., Tetrahedron Letters, vol. 5, pp. 365-368 (1973) XP002418410.
Audris Huang, et al., J. Am. Chem. Soc., vol. 126, pp. 14043-14053 (2004), XP002418411.
Masaru Ogata, et al., Eur. J. Med. Chem.—Chimica Therapeutica, vol. 16, No. 4, pp. 373-379 (1981), XP00907847
Istvan Moldvai, et al., Arch. Pharm. Pharm. Med. Chem., vol. 329, pp. 541-549 (1996) XP009078456.
Hossein Pajouheish, et al., J. Pharm. Sci., vol. 72, No. 3, pp. 318-321 (1983) XP009078411.
Krishna C. Joshi, et al., Journal of Fluorine Chemistry, vol. 44, pp. 59-72 (1989), XP002418412.
Piyasena Hewawasam, et al., Bioorganic & Medicinal Chemistry Letters, vol. 12, pp. 1023-1026 (2002), XP002418413.
Santiago Barroso, et al., J. Org., Chem., vol. 69, pp. 6821-6829 (2004) XP002418416.
Paul Aeberli, et al., J. Org. Chem., vol. 33, No. 4 pp. 1640-1643 (1968) XP002418417.
A. Walser, et al., J. Org. Chem., vol. 38, No. 3, pp. 449-456 (1973), XP002418418.
Javad Azizian, et al., Synthesis, vol. 2005, No. 7, pp. 1095-1098 (2005) XP 002418427.
Andrew Fensome, et al., Bioorganic & Medicinal Chemistry Letters, vol. 12, pp. 3487-3490 (2002), XP002418428.
T.V. Rajanbabu, et al., J. Org. Chem., vol. 51, pp. 1704-1712 (1986) XP002418429.
Karnail S. Atwal, et al., J. Med. Chem., vol. 39, pp. 304-313 (1996), XP002418430.
Balazs Volk, et al., Eur. J. Org. Chem., pp. 3991-3996 (2003), XP002418431.
Keith Smith, et al., J. Chem. Soc. Perkin Trans. 1, vol. 1999, pp. 2299-2303 (1999), XP002418432.
R.L. Hinman, et al., J. Org. Chem., vol. 29, pp. 2431-2437 (1964), XP002418433.
J. Amer. Chem. Soc (2005) 127 PG. 10130.
Hellmann, H. et al, Chemische Berichte, ISSN:009-2440, vol. 86, 1346-1361 (1953) XP002481520.
Dhigemori, H. et al, Che. Abstracts Service XP002481522 (2003).
Alarcon-Vargas, D et al, Carcinogenesis, 23(4):541-547 (2002) XP002481521.
Arndt, Hans-Dieter, Kleine Molekule pp. 4664-4673—XP-002465843 (2006).
Lippa,Blaise, Bioorganic & Medicinal Chemistry Letters 18, (2008) 3359-3363.
Ding, Journal of Medicinal Chemistry (2006), 49(12), 3432-3435.
Chosez, L., Tetrahedron, (1995) 11021-11042.
Ashimori A. Journal of Organic Chem 57: 17 (2002) 4571-4572 XP002527583.
Ashimori A. Journal of American Chem Society 120 (1998) 6477-6477-6487 XP001038246.
Johnson R.S., Journal of American Chem Society (1900) 796-800 xp002156747.
Ding, Tetrahedron Letters (2005), 46 (35), 5949-5951SUN.
Shangary, Molecular Cancer Therapeutics (2008), 7(6) 1533-1542.
Shangary, Proceedings of National Academy of Science (2008) 105(10) 3933-3938.
Saddler, Blood (2008) 111(3), 1584-1593.

* cited by examiner

SPIROINDOLINONE PYRROLIDINES

PRIORITY TO RELATED APPLICATION(S)

This application claims the benefit of U.S. Provisional Application No. 61/328,711, filed Apr. 28, 2010, which is hereby incorporated by reference in its entirety.

SUMMARY OF THE INVENTION

The present invention relates to spiroindolinone pyrrolidines I which act as antagonists of mdm2 interactions and hence are useful as potent and selective anticancer agents. The present compounds are of the general formula

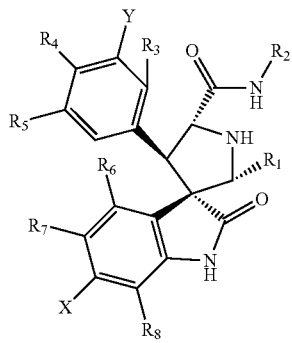

wherein X, Y and $R_1$ to $R_8$ are as described herein and the enantiomers and pharmaceutically acceptable salts and esters thereof.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

DETAILED DESCRIPTION OF THE INVENTION

The present invention relates to spiroindolinone pyrrolidine derivatives I which act as antagonists of mdm2 interactions and hence are useful as potent and selective anticancer agents. The present compounds are of the general formula

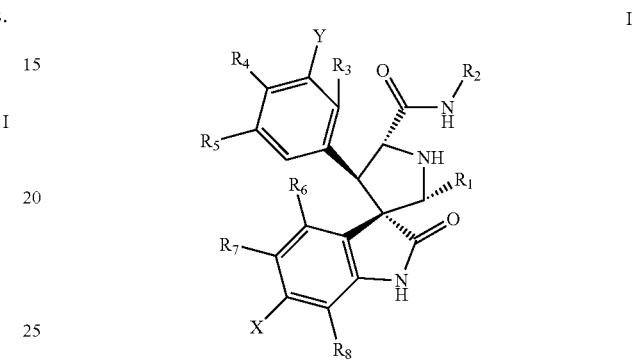

wherein
X is selected from the group consisting of F, Cl, and Br;
Y is selected from the group consisting of F, Cl, and Br;
$R_1$ is a substituted lower alkyl selected from

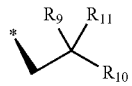

where $R_9$, $R_{10}$ are both methyl, or linked to form a cyclopropyl, cyclobutyl, cyclopentyl or cyclohexyl group;
$R_{11}$ is $(CH_2)_q$—$R_{12}$;
$R_{12}$ is selected from hydrogen, hydroxyl, lower alkyl, lower alkoxy, lower cycloalkenyl, substituted cycloalkenyl, lower cycloalkyl, substituted cycloalkyl, aryl, substituted aryl, hetereoaryl, substituted heteroaryl, hetereocycle or substituted heterocycle;
q is 0, 1 or 2;
$R_2$ is selected from the group consisting of aryl, substituted aryl, heteroaryl and substituted heteroaryl;
$R_3$, $R_4$, $R_5$ is selected from H or F with the proviso that at least two of $R_3$, $R_4$, $R_5$ are hydrogen;
$R_6$, $R_7$, $R_8$ is selected from H or F with the proviso that at least two of $R_6$, $R_7$, $R_8$ are hydrogen and the pharmaceutically acceptable salts and enantiomers thereof.

More preferred are compounds of formula I
wherein,
X is selected from F, Cl or Br;
Y is selected from F, Cl or Br;
$R_1$ is

$R_2$ is selected from aryl, substituted aryl, heteroaryl and substituted heteroaryl having the formulas

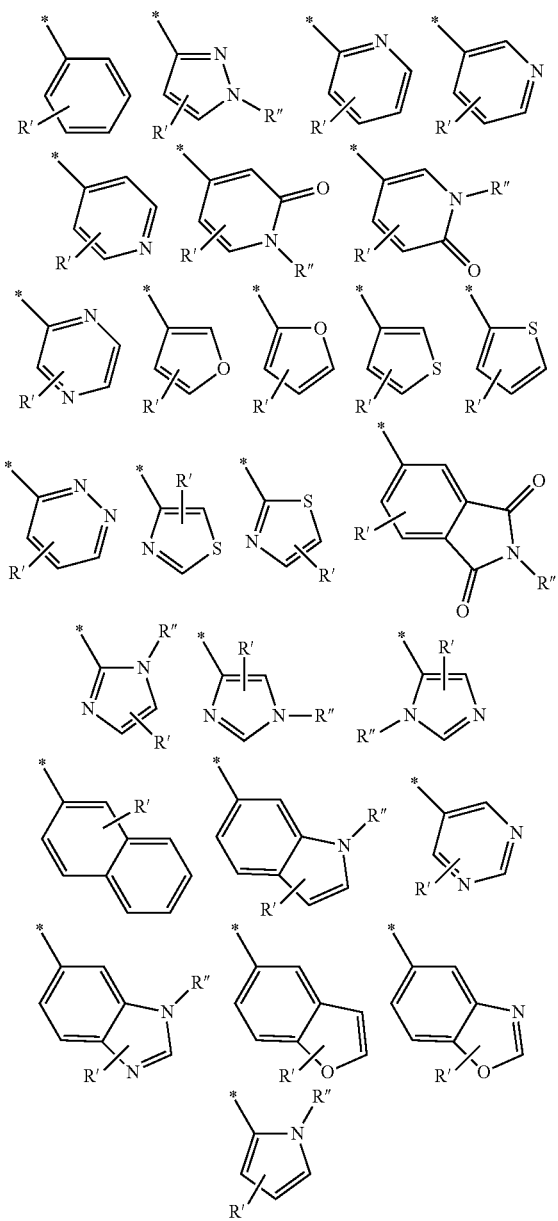

R' is 1-5 groups, preferably 1-3 groups independently selected from hydrogen, lower alkyl, lower-alkenyl, lower-alkynyl, dioxo-lower-alkylene (forming e.g. a benzodioxyl group), halogen, hydroxy, CN, CF$_3$, NH$_2$, N(H, lower-alkyl), N(lower-alkyl)$_2$, aminocarbonyl, lower-alkylaminocarbonyl, carboxy, NO$_2$, lower-alkoxy, thio-lower-alkoxy, lower-alkylsufonyl, aminosulfonyl, lower-alkylcarbonyl, lower-alkyl-carbonyloxy, lower-alkoxycarbonyl, lower-alkyl-carbonyl-NH, fluoro-lower-alkyl, fluoro-lower-alkoxy, lower-alkoxycarbonyl-lower-alkoxy, carboxy-lower-alkoxy, carbamoyl-lower-alkoxy, hydroxy-lower-alkoxy, NH$_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, NH$_2$, N(H, lower-alkyl) or N(lower-alkyl)$_2$ R" is one group selected from hydrogen, lower alkyl, lower-alkenyl, lower-alkynyl, hydroxy, CN, CF$_3$, aminocarbonyl, carboxy, lower-alkoxy, thio-lower-alkoxy, lower-alkylsufonyl, aminosulfonyl, lower-alkylcarbonyl, lower-alkoxycarbonyl, lower-alkoxycarbonyl, fluoro-lower-alkyl, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, NH$_2$, N(H, lower-alkyl) or N(lower-alkyl)$_2$ $R_3$, $R_4$, $R_5$ is selected from H or F with the proviso that at least two of $R_3$, $R_4$, $R_5$ are hydrogen;

$R_6$, $R_7$, $R_8$ is selected from H or F with the proviso that at least two of $R_6$, $R_7$, $R_8$ are hydrogen and the pharmaceutically acceptable salts and enantiomers thereof.

Further preferred are compounds of formula I in which
X is F, Cl or Br;
Y is F, Cl or Br;
$R_1$ is

$R_2$ is selected from

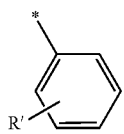

R' is 1-3 groups independently selected from hydrogen, lower alkyl, halogen, hydroxy, CN, CF$_3$, NH$_2$, N(H, lower-alkyl), N(lower-alkyl)$_2$, aminocarbonyl, lower-alkylaminocarbonyl, carboxy, NO$_2$, lower-alkoxy, thio-lower-alkoxy, lower-alkylsufonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxycarbonyl-lower-alkoxy, carboxy-lower-alkoxy, carbamoyl-lower-alkoxy, hydroxy-lower-alkoxy, NH$_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, NH$_2$, N(H, lower-alkyl) or N(lower-alkyl)$_2$ $R_3, R_4, R_5$ is selected from H or F with the proviso that at least two of $R_3, R_4, R_5$ are hydrogen; and $R_6, R_7, R_8$ is selected from H or F with the proviso that at least two of $R_6, R_7, R_8$ are hydrogen.

Especially preferred are compounds selected from the group consisting of rac-4-{[(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidin]e-5'-carbonyl]-amino}-3-methoxy-benzoic acid methyl ester, rac-4-{[(2'R,3'S,4'S,5'R)-6-chloro-4'-(3-chloro-2-fluoro-phenyl)-2'-(2,2-dimethyl-propyl)-7-fluoro-2-oxo-1,2-di-hydro-spiro [indole-3,3'-pyrrolidin]e-5'-carbonyl]-amino}-3-methoxy-benzoic acid methyl ester, chiral(2'R,3'S,4'S,5'R)-6-chloro-4'-(3-chloro-2-fluoro-phenyl)-2'-(2,2-dimethyl-propyl)-2-oxo-1,2-dihydro-spiro [indole-3,3'-pyrrolidine]-5'-carboxylic acid (4-carbamoyl-phenyl)-amide, chiral 4-{[(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidin]e-5'-carbonyl]-amino}-3-methoxy-benzoic acid, chiral(2'R,3'S,4'S,5'R)-6-chloro-4'-(3-chloro-2-fluoro-phenyl)-2'-(2,2-dimethyl-propyl)-2-oxo-1,2-dihydro-spiro [indole-3,3'-pyrrolidine]-5'-carboxylic acid[4-(2-hydroxy-ethoxy)-2-methoxy-phenyl]-amide and chiral(2'R,3'S,4'S,5'R)-6-Chloro-4'-(3-chloro-2-fluoro-phenyl)-2'-(2,2-dimethyl-propyl)-2-oxo-1,2-dihydro-spiro [indole-3,3'-pyrrolidine]-5'-carboxylic acid (4-carbamoyl-2-methoxy-phenyl)-amide.

TERMS & DEFINITIONS

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkyl-sufonyl, aminosulfonyl, lower-alkylcarbonyl, lower-alkyl-carbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkyl-sulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the cycloalkyl, cycloalkenyl, aryl, heteroaryl and heterocycle rings are halogen, lower alkoxy, lower alkyl, hydroxycarbonyl, carboxy, carboxy lower alkoxy, oxo and CN. Preferred substituents for alkyl are alkoxy and N(lower alkyl)$_2$.

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 6, preferably 2 to 4 carbon atoms. Examples of such "alkenyl group" are vinyl, ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, bromine, or iodine, preferably, fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both may be substituted or unsubstituted.

"Heterocycle" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like.

Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formula I as well as their salts that have at least one asymmetric carbon atom may be present as racemic mixtures or different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

The compounds of the present invention are useful in the treatment or control of cell proliferative disorders, in particular oncological disorders. These compounds and formulations containing said compounds may be particularly useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration; it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"IC50" refers to the concentration of a particular compound required to inhibit 50% of a specific measured activity. $IC_{50}$ can be measured, inter alia, as is described subsequently.

Synthetic Methods

The present invention provides novel methods for the synthesis of spiroindolinones of formula I. Compounds of this invention can be synthesized according to the following general schemes. Suitable processes for synthesizing these compounds are provided in the examples.

Preparations of intermediates II and III are illustrated in Scheme 1 and 2. In general an appropriately selected aldehyde can be reacted with glycine tert-butyl ester to generate imine II and were used as a crude product (Scheme 1).

Scheme 1

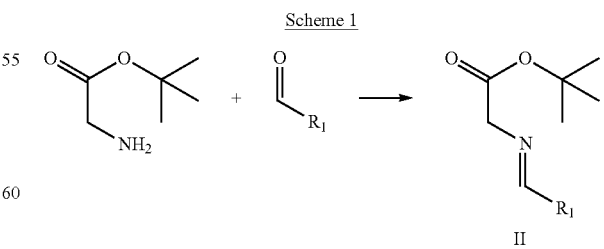

Reagents and conditions:
$CH_2Cl_2$, room temperature, 3 h

An intermediate of formula III can be made from a base-catalyzed condensation reaction of appropriately selected substituted 2-oxindole and substituted benzaldehyde in methanol. The choice of bases includes but is not limited to pyrrolidine or piperidine. The reaction generates III as a mixture of Z- and E-isomers with E-isomer as the major product.

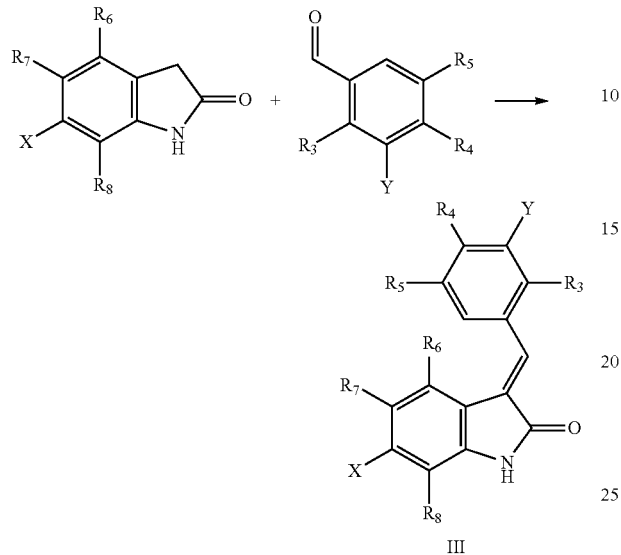

Reagents and conditions:
pyrrolidine or piperidine, MeOH, 50° C., 3 h

As illustrated in Scheme 3, spiroindolinones of formula IV and its enantiomer IV' as a racemic mixture can be made from intermediates II and III by the 1,3-dipolar cycloaddition reaction mediated by lewis acid AgF and triethylamine. The [2+3] cycloaddition reactions of azomethine ylides 1,3-dipoles with olefinic dipolarphiles to form pyrrolidine ring formation have been described in published procedures including Jorgensen, K. A. et al (*Org. Lett.* 2005, Vol 7, No. 21, 4569-4572), Grigg, R. et al (*Tetrahedron*, 1992, Vol 48, No. 47, 10431-10442; *Tetrahedron*, 2002, Vol 58, 1719-1737), Schreiber, S. L. et al (*J. Am. Chem. Soc.*, 2003, 125, 10174-10175), and Carretero, J. C. et al (*Tetrahedron*, 2007, 63, 6587-6602). Racemic mixtures of compounds IV and IV' are subsequently converted to racemic mixture of acid V and V' by deprotection reaction using trifluoroacetic acid, followed by amide formation with various aryl or heteroaryl amines using diphenylphsphinic chloride as the coupling reagent to give the racemic mixture of compounds in formula I and I'.

Scheme 3

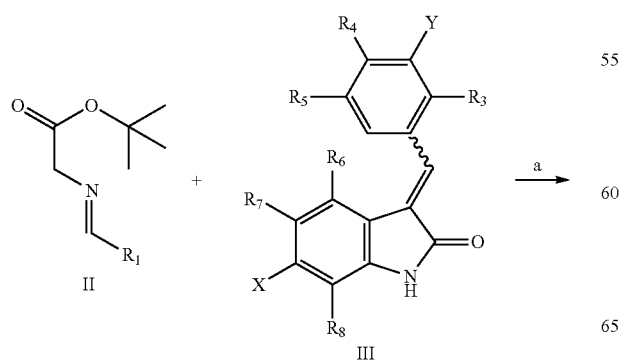

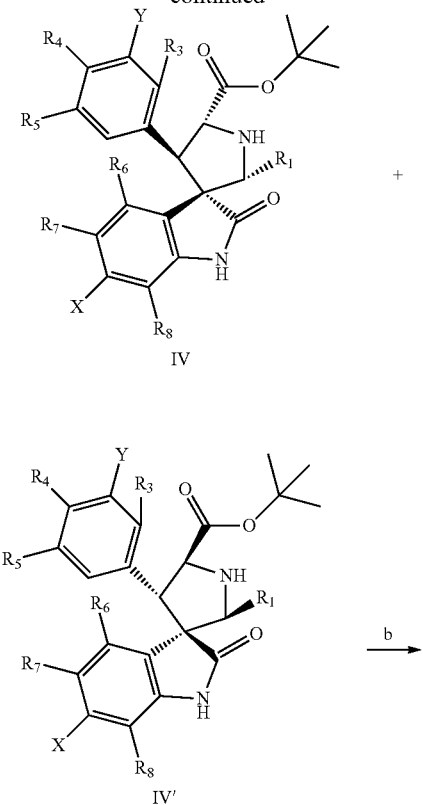

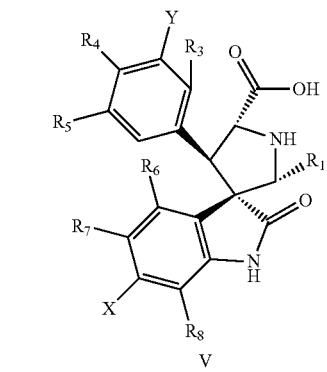

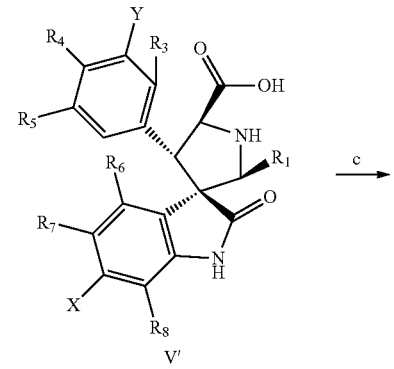

-continued

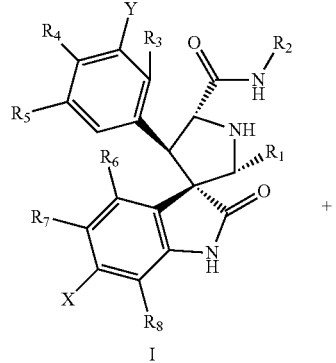

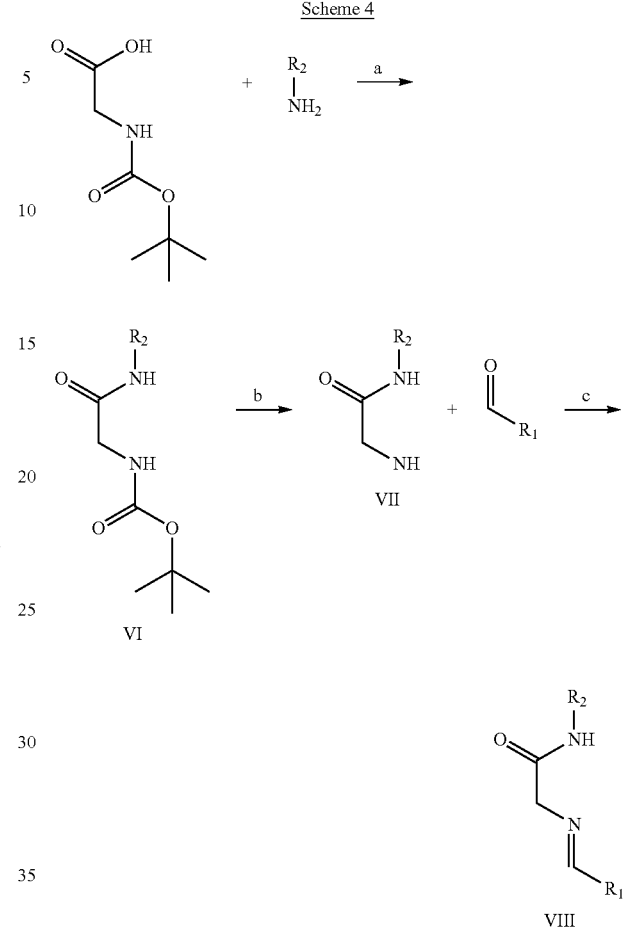

Scheme 4

Reagents and conditions:
a. AgF, NEt₃, CH₂Cl₂ or ClCH₂CH₂Cl, rt, 18 h;
b. TFA, CH₂Cl₂, rt, 18 h;
c. NH₂R₂, dipenylphosphinic chloride, iPr₂NEt, CH₂Cl₂ or ClCH₂CH₂Cl, rt, 18 h;

Alternatively, racemic synthesis of compounds in formula I can be achieved as outlined in Scheme 4. Aryl or heteroaryl amines $R_2NH_2$ can be reacted with N-protected glycine like N-Boc glycine by using a coupling condition like HATU and Hunig base to give intermediate VI. Intermediate VI can be treated with trifluoroacetic acid at room temperature to remove protective Boc group and give intermediate VII. Apropriately selected aldehyde $R_1CHO$ can react with VII to give the imine VIII under conditions similar to the method described in Scheme I. Finally, The 1,3-dipolar cycloaddition key reaction between intermediates VIII and III mediated by lewis acid AgF and triethylamine give the racemic mixture of compounds I and I' in formula I. It is conceivable that introducing a chiral auxiliary like (R)-BINAP in the presence of AgF or AgOAc and triethylamine in solvent like dichloromethane or toluene under the conditions for the 1,3-dipolar cycloaddition reaction could lead to chiral or optically enriched compounds I. Racemic mixture of compounds I and I' can be chirally chirally separated by using chiral Super Fluid Chromatography (SFC) or chiral HPLC or chiral column chromatography.

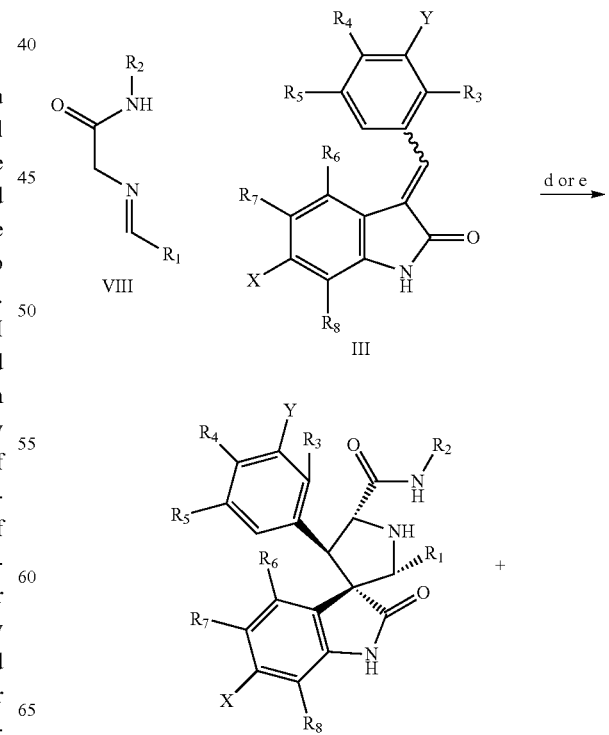

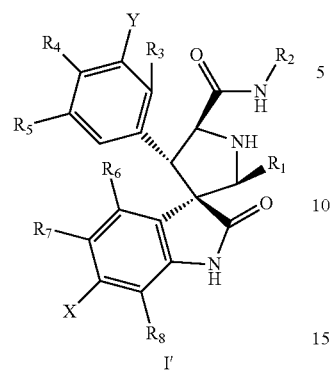

I'

Reagents and conditions:
a. HATU, iPr₂NEt, CH₂Cl₂, rt, 18 h;
b. TFA, CH₂Cl₂, rt, 1 h;
c. CH₂Cl₂, rt, 18 h;
d. AgF, NEt₃, CH₂Cl₂, rt, 18 h;
e. AgOAc, NEt₃, (R)-BINAP, toleuene The asymmetric synthesis of compounds in formula I was outlined in Scheme 5. The chiral intermediate IX can be prepared through an asymmetric [1,3] dipolar cycloaddition reaction by following published procedures described by Wang, S., et al (*J. Am. Chem. Soc.,* 2005, 127, 10130; *J. Med. Chem.* 2006, 49, 3432; WO2006091646; WO2008036168) and Williams, R. M., et al (*J. Am. Chem. Soc.,* 2000, 122, 5666). The intermediate IX can be converted into chiral acid XI in three steps. First, catalytic hydrogenation reaction of IX, followed by reaction with trimethylsilyldiazomethane would afford chiral methyl ester X. Similar transformation has been published by Williams, R. M. (*J. Am. Chem. Soc.,* 2000, 122, 5666; *Tetrahedron,* 2004, 60(42), 9503; *Heterocycles,* 2002, 58 563). The hydrolysis of X by NaOH would lead to chiral acid XI, followed by amide formation with various aryl or heteroaryl amines R₂NH₂ using diphenylphsphinic chloride as the coupling reagent to give chiral compounds in formula I.

Scheme 5

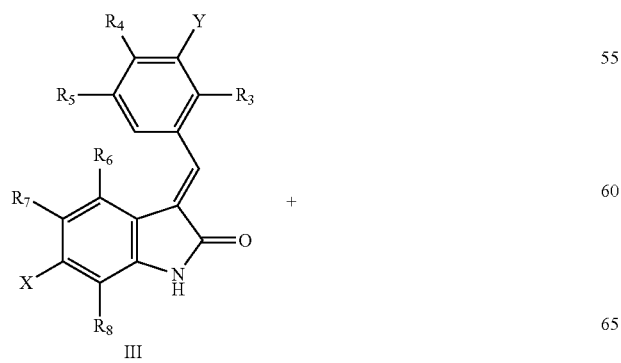

III

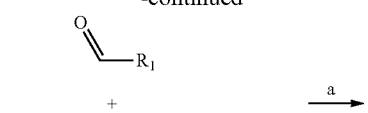

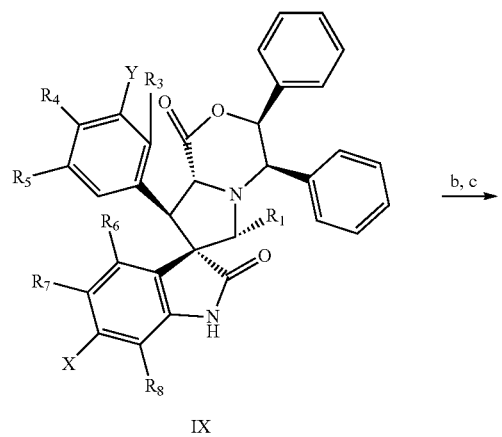

IX

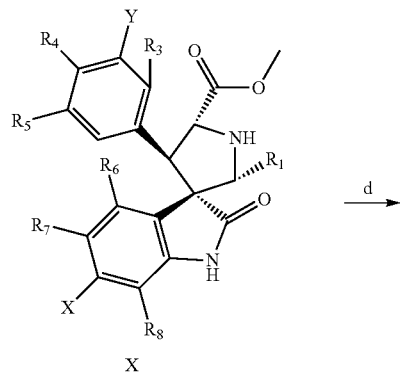

X

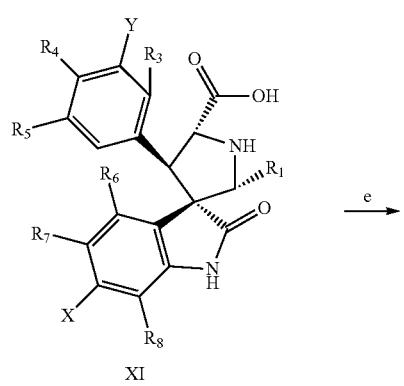

XI

-continued

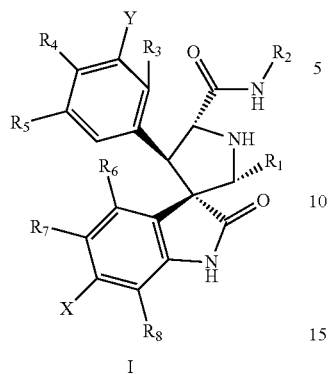

I

Reagents and conditions:
a. melecular sieves, toluene, 70° C., 18 h;
b. H₂, PdCl₂, THF/MeOH, rt, 18 h;
c. TMSCH₂N₂, MeOH, 0° C., 15 min;
d. NaOH, H₂O/THF/MeOH. rt, 3 h;
e. NH₂R₂, dipenylphosphinic chloride, iPr₂NEt, CH₂Cl₂, rt, 18 h;

EXAMPLES

The compounds of the present invention may be synthesized according to novel techniques. The following examples and references are provided to aid the understanding of the present invention, the true scope of which is set forth in the appended claims.

Example 1

Preparation of intermediate [3,3-dimethyl-but-(E)-ylideneamino]-acetic acid tert-butyl ester

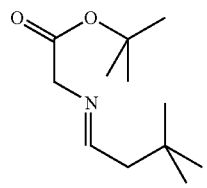

M.W. 213.32
$C_{12}H_{23}NO_2$

A mixture of glycine tert-butyl ester (Alfa) (2.71 g, 20.0 mmol) and 3,3-dimethyl-butyraldehyde (Alfa) (2.21 g, 21.0 mmol) in CH₂Cl₂ (50 mL) was stirred at rt overnight. The reaction mixture was concentrated and the residue was dried in vacuo to give [3,3-dimethyl-but-(E)-ylideneamino]-acetic acid tert-butyl ester (4.29 g, 100%) as colorless oil which was used in the next step without further purification.

Example 2

Preparation of intermediate E/Z-6-chloro-3-(3-chloro-2-fluoro-benzylidene)-1,3-dihydro-indol-2-one

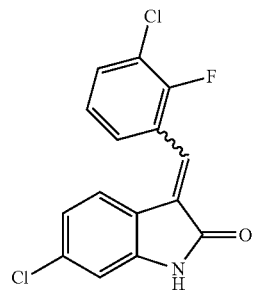

M.W. 308.14
$C_{15}H_8Cl_2FNO$

To the mixture of 6-chloro-2-oxindole (11 g, 65.6 mmol) (Crescent) and 3-chloro-2-fluorobenzaldehyde (12 g, 75.7 mmol) (Aldrich) in methanol (140 mL) was added piperidine (5.59 g, 65.6 mmol) (Aldrich) dropwise. The mixture was then heated at 50° C. for 3 h. After cooled to 4° C., the mixture was filtered and resulting precipitate was collected, dried to give E/Z-6-chloro-3-(3-chloro-2-fluoro-benzylidene)-1,3-dihydro-indol-2-one as a yellow solid (Yield 18 g, 89%).

Example 3

Preparation of intermediate rac-(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid tert-butyl ester

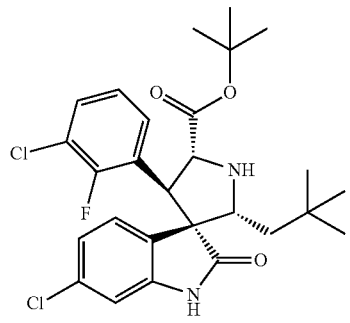

M.W. 521
$C_{27}H_{31}Cl_2FN_2O_3$

To a solution of [3,3-dimethyl-but-(E)-ylideneamino]-acetic acid tert-butyl ester (2 g, 9.4 mmol) prepared in Example 1 and E/Z-6-chloro-3-(3-chloro-2-fluoro-benzylidene)-1,3-dihydro-indol-2-one (2.3 g, 7.5 mmol) prepared in Example 2 in dichloromethane (30 mL) were added triethyl amine (2.8 mL, 20 mmol) and AgF (1.1 g, 8.7 mmol). The mixture was stirred at room temperature for 3 h. The mixture was concentrated, and the residue was partitioned between ethyl acetate and brine. The organic layer was separated, washed with water, dried over MgSO₄, and concentrated. The residue was purified by chromatography (EtOAc:hexanes=1:3, 1:2) to give as rac-(2'R,3'S,4'S,5'R)-6-chloro-4'-(3-chloro-2-fluorophenyl)-2'-(2,2-dimethyl-propyl)-2-oxo-1,2-dihydro-spiro[indole-3,3'-pyrrolidine]-5'-carboxylic acid tert-butyl ester a white foam (1.9 g, 49%)

Example 4

Preparation of intermediate rac-(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid

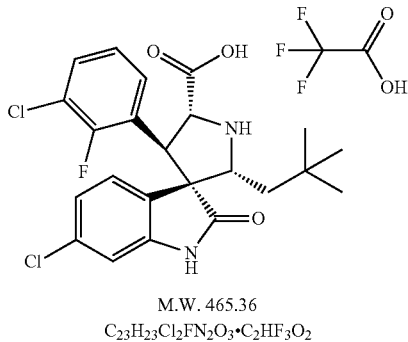

M.W. 465.36
$C_{23}H_{23}Cl_2FN_2O_3 \cdot C_2HF_3O_2$

A solution of rac-(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid tert-butyl ester (1 g, 1.9 mmol) in dichloromethane (20 mL) was added trifluoroacetic acid (10 g). The reaction mixture was stirred at room temperature for 18 h, then concentrated. The residue was then triturated with ethyl ether hexanes, concentrated, dried in vacuo to give rac-(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid as a off white solid (1.1 g, 99%).

Example 5

Preparation of rac-4-{[(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidin]e-5'-carbonyl]-amino}-3-methoxy-benzoic acid methyl ester

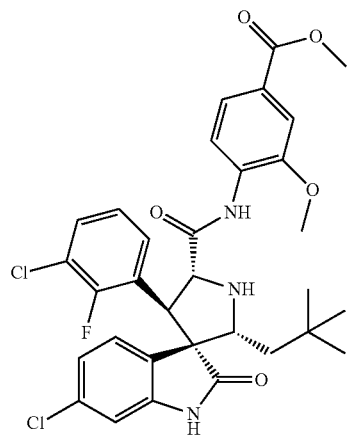

M.W. 628.53
$C_{32}H_{32}Cl_2FN_3O_5$

To a solution of rac-(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid (0.8 g, 1.38 mmol) in dichloromethane (15 mL) was added diisopropylethylamine (0.89 g, 6.9 mmol), diphenylphosphinic chloride (Aldrich) (0.65 g, 2.8 mmol) respectively. The mixture was stirred at room temperature for 8 min, then methyl 4-amino-3-methoxy-benzoate (Ark) (0.5 g, 2.8 mmol) was added. The reaction mixture was stirred at room temperature for 4 days. The mixture was concentrated. The residue was partitioned between ethyl acetate and water. The organic layer was separated, washed with water, brine, dried over $Na_2SO_4$, then concentrated. The residue was purified by chromatography (0-15% of EtOAc in $CH_2Cl_2$) to give rac-4-{[(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidin]e-5'-carbonyl]-amino}-3-methoxy-benzoic acid methyl ester as a off white solid (70 mg, 8%).

LC-MS (ES$^+$) m/z Calcd for $C_{32}H_{32}Cl_2FN_3O_5H$ [(M+H)$^+$]: 628. found: 628.

Example 6

Preparation of intermediate E/Z-6-chloro-3-(3-chloro-2-fluoro-benzylidene)-7-fluoro-1,3-dihydro-indol-2-one

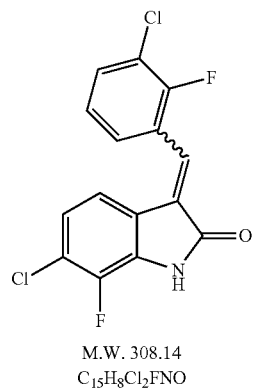

M.W. 308.14
$C_{15}H_8Cl_2FNO$

To the mixture of 6-chloro-7-fluoroindolin-2-one (1.1 g, 5.9 mmol) (Natrochem) and 3-chloro-2-fluorobenzaldehyde (1.4 g, 8.9 mmol) (Aldrich) in methanol (50 mL) was added piperidine (1.5 g, 17.8 mmol) (Aldrich) dropwise. The mixture was then heated at 50° C. for 3 h. After cooled to room temperature, the mixture was concentrated. The residue was partitioned between ethyl acetate and water. The organic layer was separated, and aqueous layer was extracted with ethyl acetate. The organic layers were combined, washed with brine, dried over $MgSO_4$, and concentrated to half its volume. The mixture was filtered and resulting precipitate was collected, dried to give the first batch of desired product (1.4 g). The filtrate was concentrated, and residue was purified by chromatography (20-40% EtOAc in hexanes) to give the second batch of desired product (0.44 g). The two batches were combined to give E/Z-6-chloro-3-(3-chloro-2-fluoro-benzylidene)-7-fluoro-1,3-dihydro-indol-2-one as a yellow solid (Yield 1.84 g, 89%).

Example 7

Preparation of rac-4-{[(2'R,3'S,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidin]e-5'-carbonyl]-amino}-3-methoxy-benzoic acid methyl ester

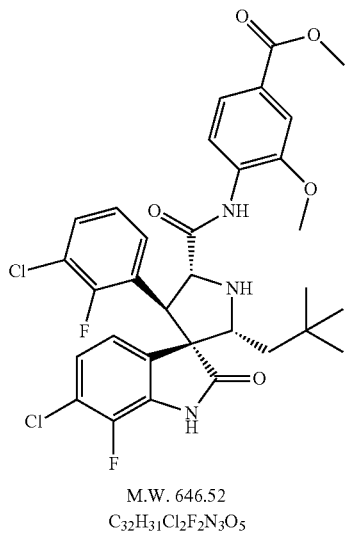

M.W. 646.52
$C_{32}H_{31}Cl_2F_2N_3O_5$

To a solution of 4-{2-[3,3-dimethyl-but-(E)-ylidene-amino]-acetylamino}-3-methoxy-benzoic acid methyl ester (0.3 g, 0.92 mmol, RO5524462-000, preparation procedure will be disclosed elsewhere) and E/Z-6-chloro-3-(3-chloro-2-fluoro-benzylidene)-7-fluoro-1,3-dihydro-indol-2-one (0.3 g, 0.92 mmol) in dichloromethane (30 mL) were added triethylamine (0.26 mL, 1.84 mmol) and AgF (0.12 g, 0.92 mmol). The mixture was stirred at room temperature for 3 h. The mixture was concentrated, and the residue was partitioned between ethyl acetate and brine. The organic layer was separated, washed with water, dried over MgSO₄, and concentrated. The residue was purified by chromatography (5-10% EtOAc in dichloremethane) to give rac-4-{[(2'R,3'S,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidin]e-5'-carbonyl]-amino}-3-methoxy-benzoic acid methyl ester as a white solid (0.19 g, 32%).

LC-MS (ES⁺) m/z Calcd for $C_{32}H_{31}Cl_2F_2N_3O_5$+H [(M+H)⁺]: 634. found: 634.

Example 8

Preparation of chiral(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid methyl ester

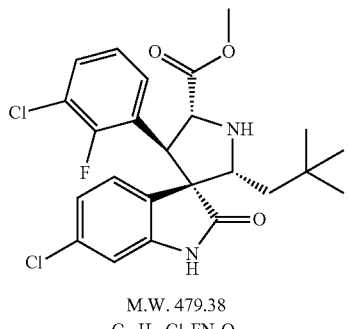

M.W. 479.38
$C_{24}H_{25}Cl_2FN_2O_3$

To a mixture of (5R,6S)-5,6-diphenylmorpholin-2-one (3.4 g, 13.4 mmol, ArkPharminc) in toluene (80 mL) was added E/Z-6-chloro-3-(3-chloro-2-fluorobenzylidene)indolin-2-one (3.5 g, 11.3 mmol) prepared in Example 2, 3,3-dimethylbutyraldehyde (1.3 g, 13.4 mmol, Aldrich). The reaction mixture was stirred at 80° C. for 18 h. The mixture was filtered through a short pad of celite. The pad was washed with additional toluene. The filtrates were combined, and concentrated. The residue was purified by chromatography (10-25% EtOAc inhexanes) to give desired 1,3-dipolar product chiral(3S,3'S,4'R,6'R,8'S,8a'R)-6-chloro-8'-(3-chloro-2-fluorophenyl)-6'-neopentyl-3',4'-diphenyl-3',4',8',8a'-tetrahydrospiro[indoline-3,7'-pyrrolo[2,1-c][1,4]oxazine]-1',2(6'H)-dione as a yellow foam (Yield, 5.7 g, 66%).

To a solution of chiral(3S,3'S,4'R,6'R,8'S,8a'R)-6-chloro-8'-(3-chloro-2-fluorophenyl)-6'-neopentyl-3',4'-diphenyl-3',4',8',8a'-tetrahydrospiro[indoline-3,7'-pyrrolo[2,1-c][1,4]oxazine]-1',2(6'H)-dione (3.5 g, 5.4 mmol) in terahydrofuran (30 mL) and methanol (30 mL) was added PdCl₂ (3 g, 17 mmol). The container was flushed with hydrogen before finally pressurizing to 60 psi. The reaction suspension was vigorously shaken in a Parr under hydrogen atmosphere for 18 h. TLC analysis indicated the complete consumption of starting material and formation of the product. The mixture was filtered through a shord pad of celite. The filtrate concentrated, and the residue was dissolved in methanol (10 mL) and dichlormethane (10 mL). To the solution was added an ethyl ether (2 M, Aldrich) solution of (trimethylsilyl)diazomethane (2.7 mL, 5.4 mmol) until a yellow color persisted. The reaction mixture was stirred at room temperature for 10 min. The mixture was concentrated, and the residue was purified by chromatography (15-25-40% EtOAc in hexanes) to give chiral(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid methyl ester as a white foam (1.3 g, 50%)

Example 9

Preparation of chiral(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid

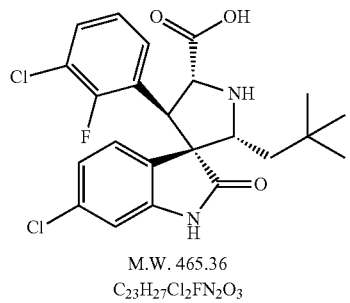

M.W. 465.36
$C_{23}H_{27}Cl_2FN_2O_3$

To a solution of chiral(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid methyl ester (1.2 g, 2.5 mmol) in tetrahydrofuran (30 mL) was added an aqueous solution (1 N) of NaOH (12.5 mL, 12.5 mmol) and methanol (10 mL). The reaction mixture was stirred at room temperature for 3 h, and then cooled to room temperature. The "pH" of the mixture was adjusted to 5-6 by aqueous HCl solution, then concentrated to a small volume. The residue was partitioned between ethyl acetate and water. The organic layer was separated, and the aqueous layer was extracted with ethyl acetate twice. The organic extracts were combined, washed with water, brine, dried over MgSO₄, and concentrated to give chiral(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid as a white solid (1.1 g, 94%).

Example 10

Preparation of chiral(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide

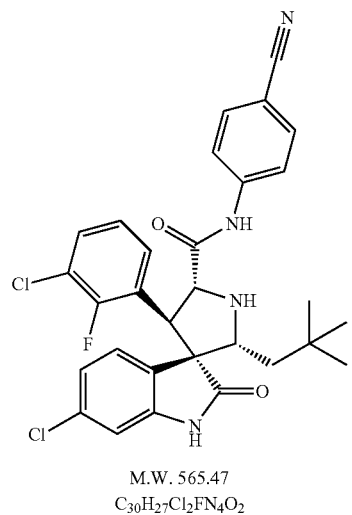

M.W. 565.47
C₃₀H₂₇Cl₂FN₄O₂

To a solution of chiral(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (1 g, 2.2 mmol) in dichloromethane (10 mL) was added diisopropylethylamine (1.1 g, 8.6 mmol), diphenylphosphinic chloride (Aldrich) (1 g, 4.3 mmol) respectively. The mixture was stirred at room temperature for 15 min, then 4-aminobenzonitrile (Aldrich) (0.25 g, 2.2 mmol) was added. The reaction mixture was stirred at room temperature for 18 h. The mixture was concentrated. The residue was partitioned between ethyl acetate and water. The organic layer was separated, washed with water, brine, dried over Na₂SO₄, then concentrated. The residue was purified by chromatography (20% of EtOAc in CH₂Cl₂) to give chiral(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide as a off white solid (130 mg, 7%).

LC-MS (ES⁺) m/z Calcd for C₃₀H₂₇Cl₂FN₄O₂+H [(M+H)⁺]: 565. found: 565.

Example 11

Preparation of chiral(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide

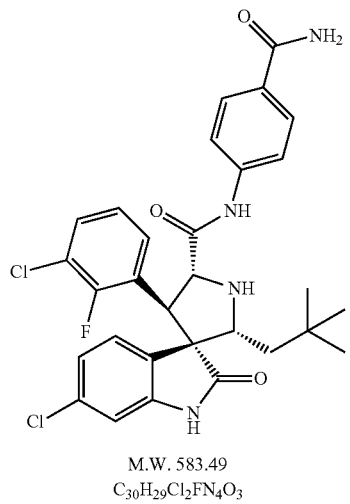

M.W. 583.49
C₃₀H₂₉Cl₂FN₄O₃

To the solution of chiral(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide (0.13 g, 0.23 mmol) in DMSO (5 mL) at 0° C. was added an aqueous solution (30% Aldrich) of H₂O₂ (0.26 g, 2.3 mmol), then aqueous solution (1 N) of NaOH (0.69 mL, 0.69 mmol) was added dropwise. The reaction mixture was stirred at 0° C. for 15 min. The mixture was partitioned between ethyl acetate and saturated aqueous Na₂SO₃ solution. The organic layer was separated, washed with water, brine, dried over MgSO₄, and concentrated. The residue was purified by chromatography (50-100% EtOAc in CH₂Cl₂) to give chiral(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide as a white solid (Yield 30 mg, 22%).

LC-MS (ES⁺) m/z Calcd for C₃₀H₂₉Cl₂FN₄O₃+H [(M+H)⁺]: 583. found: 583.

Example 12

Preparation of chiral 4-{[(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidin]e-5'-carbonyl]-amino}-3-methoxy-benzoic acid

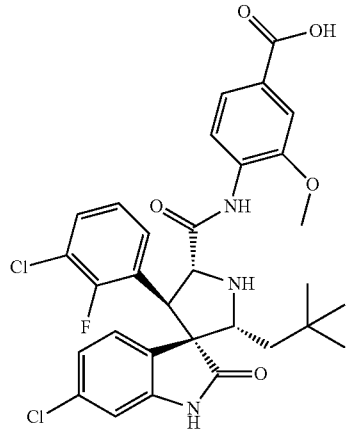

M.W. 614.50
C₃₁H₃₀Cl₂FN₃O₅

To a solution of chiral chiral 4-{[(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidin]e-5'-carbonyl]-amino}-3-methoxy-benzoic acid methyl ester (0.1 g, 0.16 mmol) in tetrahydrofuran (9 mL) was added an aqueous solution (1 N) of NaOH (6 mL, 6 mmol) and methanol (3 mL). The reaction mixture was stirred at room temperature for 5 h. The "pH" of the mixture was adjusted to 5-6 by aqueous HCl solution, then concentrated to a small volume. The residue was partitioned between ethyl acetate and water. The organic layer was separated, and the aqueous layer was extracted with ethyl acetate twice. The organic extracts were combined, washed with water, brine, dried over MgSO$_4$, and concentrated to give chiral 4-{[(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidin]e-5'-carbonyl]-amino}-3-methoxy-benzoic acid as a white solid (60 mg, 61%).

LC-MS (ES$^+$) m/z Calcd for $C_{31}H_{30}Cl_2FN_3O_5$+H [(M+H)$^+$]: 614. found: 614.

Example 13

Preparation of intermediate 4-[2-(tert-butyl-dimethyl-silanyloxy)-ethoxy]-2-methoxy-phenylamine

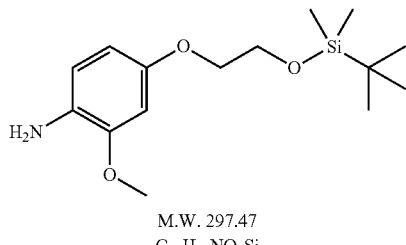

M.W. 297.47
$C_{15}H_{27}NO_3Si$

Step a: To a solution of 4-fluoro-2-methoxy-1-nitrobenzene (Combi-blocks, 3.4 g, 19.9 mmol) in DMSO (40 mL) was added an aqueous solution (1 N) of NaOH (40 mL, 40 mmol). The reaction mixture was heated at 80° C. for 20 h. The mixture was cooled to room temperature, and the "pH" of the solution was adjusted to 5 by aqueous HCl solution. The mixture was extracted with ethyl acetate three times. The combined organic extract was washed with water, brine, dried over MgSO$_4$, and concentrated to give 3-methoxy-4-nitrophenol as a light yellow solid (3.2 g, 95%).

Step b: To a solution of 3-methoxy-4-nitrophenol (1 g, 5.9 mmol) in anhydrous DMF (25 mL) were added K$_2$CO$_3$ (2.45 g, 17.7 mmol) and (2-bromoethoxy)(tert-butyl)dimethylsilane (1.7 g, 7.1 mmol) sequentially. The reaction mixture was heated at 70° C. for 20 h. The mixture was cooled to room temperature, and diluted with water. The mixture was extracted with ethyl acetate three times. The combined organic extract was washed with water, brine, dried over MgSO$_4$, and concentrated. The residue was purified by chromatography (0-20% EtOAc in hexanes) to give tert-butyl-[2-(3-methoxy-4-nitro-phenoxy)-ethoxy]-dimethyl-silane as a light yellow oil (1.0 g, 52%).

Step c: A suspension of tert-butyl-[2-(3-methoxy-4-nitro-phenoxy)-ethoxy]-dimethyl-silane (1 g, 3.05 mmol) and Pd/C (Aldrich, 10%, 0.1 g) in ethyl acetate (25 mL) was vigorously shaken in a Parr under atmosphere of H$_2$ (50 psi) for 0.5 h. The mixture was filtered through a short pad of celite. The filtrate was concentrated to give 4-[2-(tert-butyl-dimethyl-silanyloxy)-ethoxy]-2-methoxy-phenylamine as a light yellow oil (0.9 g, 99%).

Example 14

Preparation of chiral(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid[4-(2-hydroxy-ethoxy)-2-methoxy-phenyl]-amide

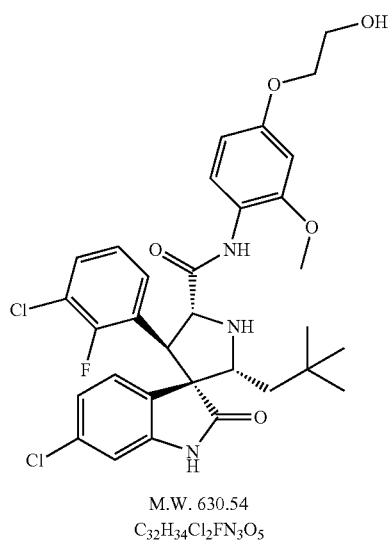

M.W. 630.54
$C_{32}H_{34}Cl_2FN_3O_5$

To a solution of chiral(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (0.16 g, 0.28 mmol) in dichloromethane (3 mL) was added diisopropylethylamine (0.18 g, 1.4 mmol), diphenylphosphinic chloride (Aldrich, 0.13 g, 0.55 mmol) respectively. The mixture was stirred at room temperature for 8 min, then 4-[2-(tert-butyl-dimethyl-silanyloxy)-ethoxy]-2-methoxy-phenylamine (0.12 g, 0.42 mmol) was added. The reaction mixture was stirred at room temperature for 18 h. The mixture was concentrated. The residue was dissolved into tetrahydrofuran (5 mL), and an aqueous solution (1 N) of HCl (1 mL, 1 mmol) was added. The reaction mixture was stirred at room temperature for 1 h, then concentrated. The residue was partitioned between ethyl acetate and water. The organic layer was separated, and aqueous layer was extracted with ethyl acetate twice. The combined organic extract was washed with water, brine, dried over Na$_2$SO$_4$, then concentrated. The residue was purified by chromatography (10-100% of EtOAc in CH$_2$Cl$_2$) to give chiral(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-2-methoxy-phenyl]-amide as a off white solid (28 mg, 16%).

MS (ES$^+$) m/z Calcd for $C_{32}H_{34}Cl_2FN_3O_5$+H [(M+H)$^+$]: 630. found: 630.

Example 15

Preparation of intermediate 4-amino-3-methoxy-benzonitrile

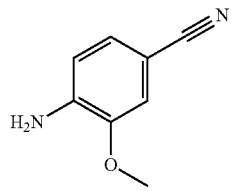

M.W. 148.17
$C_8H_8N_2O$

Step a: A mixture of 3-methoxy-4-nitrobenzoic acid (Acros, 10 g, 51 mmol) in thionyl chloride (36 g) was heated at reflux for 2 h. The mixture was concentrated. To the residue was added a methanolic solution (7 N) of ammonia. The reaction mixture was stirred at room temperature for 72 h. The mixture was concentrated, and the residue was partitioned between ethyl acetate and water. The precipitate between the two layers was filtered and collected to give 3-methoxy-4-nitrobenzamide as a light yellow solid (8 g, 81%).

Step b: To a solution of 3-methoxy-4-nitrobenzamide (8 g, 41 mmol) in dioxane (300 mL) was added pyridine (32 g, 408 mmol), followed by dropwise addition of trifluoroacetic anhydride (43 g, 204 mmol). The reaction mixture was stirred at room temperature for 5 h. Water was added to quench the reaction. The mixture was concentrated, then the residue was partitioned between ethyl acetate and water. The organic layer was separated, the aqueous layer was extracted with ethyl acetate. The organic layers were combined, washed with water, aqueous saturated $CuSO_4$ solution, brine, dried over $MgSO_4$, and concentrated to give 3-methoxy-4-nitrobenzonitrile as a off white solid (6.5 g, 90%)

Step c: To the suspension of 3-methoxy-4-nitrobenzonitrile (11.4 g, 64 mmol) in ethyl acetate (60 mL) was added 10% Pd/C (1 g). The reaction mixture was vigorously shaken in a Parr under an atmosphere of hydrogen (50 psi) at room temperature for 45 min. The mixture was filtered through a short pad of celite, and the filtrate was concentrated to give 4-amino-3-methoxy-benzonitrile as a yellow oil, which solidified at stand (9.5 g, 95%)

Example 16

Preparation of chiral(2'R,3'S,4'S,5'R)-6-Chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide

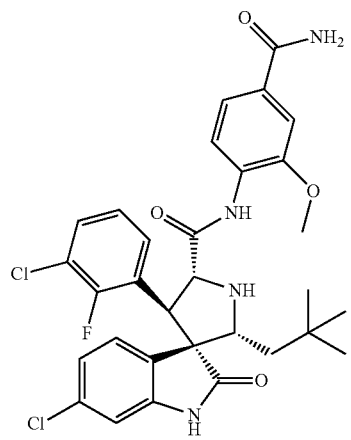

M.W. 613.51
$C_{31}H_{31}Cl_2FN_4O_4$

To a solution of chiral chiral (2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (1 g, 2.1 mmol) in dichloromethane (20 mL) was added diisopropylethylamine (1 g, 7.7 mmol), diphenylphosphinic chloride (Aldrich) (1.2 g, 5.1 mmol) respectively. The mixture was stirred at room temperature for 8 min, then 4-amino-3-methoxy-benzonitrile (0.56 g, 3.8 mmol) was added. The reaction mixture was stirred at room temperature for 66 h. The mixture was concentrated. The residue was partitioned between ethyl acetate and water. The organic layer was separated, washed with water, brine, dried over $Na_2SO_4$, then concentrated. The residue was purified by chromatography (15% of EtOAc in $CH_2Cl_2$) to give crude chiral(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide (0.14 g) which was used directly to the next step.

To a solution of crude chiral(2'R,3'S,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide (0.14 g, 0.23 mmol) in DMSO (5 mL) at 0° C. was added an aqueous solution (30% Aldrich) of $H_2O_2$ (0.24 g, 2.4 mmol), followed by the addition of aqueous solution (1 N) of NaOH (0.7 mL, 0.7 mmol). The reaction mixture was stirred at 0° C. for 15 min. The mixture was partitioned between ethyl acetate and saturated aqueous $Na_2SO_3$ solution. The organic layer was separated, washed with water, brine, dried over $MgSO_4$, and concentrated. The residue was purified by chromatography (15% of EtOAc in $CH_2Cl_2$) to give chiral chiral (2'R,3'S,4'S, 5'R)-6-Chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide as a white solid (90 mg, 6% for two steps)

LC-MS ($ES^+$) m/z Calcd for $C_{31}H_{31}Cl_2FN_4O_4$+H [(M+H)$^+$]: 613. found: 613.

Example 17

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53. Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

Activity data for the Example products expressed as $IC_{50}$: bsa:0.02% are as follows:

| Example Number | $IC_{50}$:bsa:0.02% |
| --- | --- |
| 5 | 1.951 |
| 7 | 0.828 |
| 10 | 0.15 |
| 11 | 0.136 |
| 13 | 0.121 |
| 15 | 0.097 |

What is claimed:

1. A compound of the formula

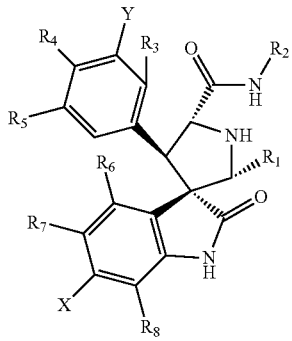

I wherein
X is selected from the group consisting of F, Cl, and Br;
Y is selected from the group consisting of F, Cl, and Br;
$R_1$ is a substituted lower alkyl selected from

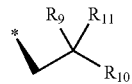

where $R_9$, $R_{10}$ are both methyl, or linked to form a cyclopropyl, cyclobutyl, cyclopentyl or cyclohexyl group;
$R_{11}$ is $(CH_2)_q$—$R_{12}$;
$R_{12}$ is selected from hydrogen, hydroxyl, lower alkyl, lower alkoxy, lower cycloalkenyl, substituted cycloalkenyl, lower cycloalkyl, substituted cycloalkyl, aryl, substituted aryl, hetereoaryl, substituted heteroaryl, hetereocycle or substituted heterocycle;
q is 0, 1 or 2;
$R_2$ is selected from the group consisting of aryl, substituted aryl, heteroaryl and substituted heteroaryl;
$R_3$, $R_4$, $R_5$ is selected from H or F with the proviso that at least two of $R_3$, $R_4$, $R_5$ are hydrogen;
$R_6$, $R_7$, $R_8$ is selected from H or F with the proviso that at least two of $R_6$, $R_7$, $R_8$ are hydrogen
and the pharmaceutically acceptable salts and enantiomers thereof.

2. The compound of claim 1 wherein
X is selected from F, Cl or Br;
Y is selected from F, Cl or Br;

$R_1$ is

$R_2$ is selected from aryl, substituted aryl, heteroaryl or substituted heteroaryl having the formulas

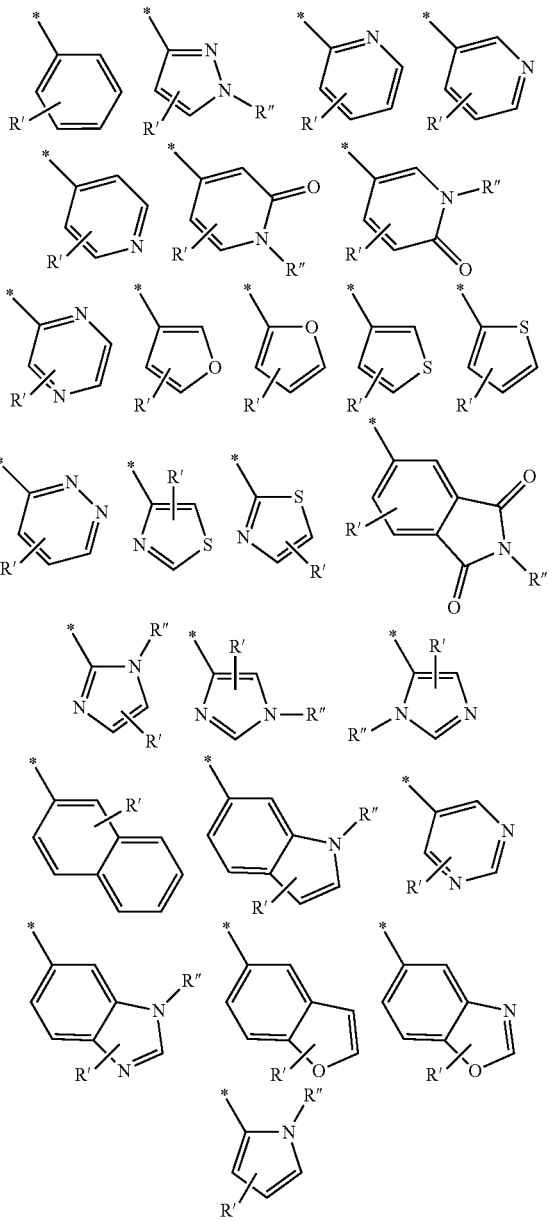

wherein R' is 1-5 groups independently selected from hydrogen, lower alkyl, lower-alkenyl, lower-alkynyl, dioxo-lower-alkylene, halogen, hydroxy, CN, $CF_3$, $NH_2$, N(H, lower-alkyl), N(lower-alkyl)$_2$, aminocarbonyl, lower-alkylaminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$;

R″ is selected from hydrogen, lower alkyl, lower-alkenyl, lower-alkynyl, hydroxy, CN, $CF_3$, aminocarbonyl, carboxy, lower-alkoxy, thio-lower-alkoxy, lower-alkylsulfonyl, aminosulfonyl, lower-alkylcarbonyl, lower-alkoxycarbonyl, fluoro-lower-alkyl, lower-alkyl-1-oxiranyl-lower-alkoxy-lower-alkyl, 2-oxo-pyrrolidin-1-yl, (1,1-dioxo)-2-isothiazolidine, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl or lower-alkyl which can optionally be substituted with halogen, hydroxy, $NH_2$, N(H, lower-alkyl) or N(lower-alkyl)$_2$;

$R_3, R_4, R_5$ is selected from H or F with the proviso that at least two of $R_3, R_4, R_5$ are hydrogen;

$R_6, R_7, R_8$ is selected from H or F with the proviso that at least two of $R_6, R_7, R_8$ are hydrogen and the pharmaceutically acceptable salts and enantiomers thereof.

3. The compound of claim 2 wherein
X is F, Cl or Br;
Y is F, Cl or Br;
$R_1$ is

$R_2$ is selected from

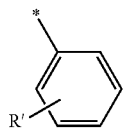

R' is 1-3 groups independently selected from hydrogen, lower alkyl, halogen, hydroxy, CN, $CF_3$, $NH_2$, N(H, lower-alkyl), N(lower-alkyl)$_2$, aminocarbonyl, lower-alkylaminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$;

$R_3, R_4, R_5$ is selected from H or F with the proviso that at least two of $R_3, R_4, R_5$ are hydrogen; and $R_6, R_7, R_8$ is selected from H or F with the proviso that at least two of $R_6, R_7, R_8$ are hydrogen.

4. A compound of claim 1 selected from the group consisting of rac-4-{[(2′R,3′S,4′S,5′R)-6-chloro-4′-(3-chloro-2-fluoro-phenyl)-2′-(2,2-dimethyl-propyl)-2-oxo-1,2-dihydro-spiro[indole-3,3′-pyrrolidin]e-5′-carbonyl]-amino}-3-methoxy-benzoic acid methyl ester, rac-4-{[(2′R,3′S,4′S,5′R)-6-chloro-4′-(3-chloro-2-fluoro-phenyl)-2′-(2,2-dimethyl-propyl)-7-fluoro-2-oxo-1,2-dihydro-spiro[indole-3,3′-pyrrolidin]e-5′-carbonyl]-amino}-3-methoxy-benzoic acid methyl ester, chiral (2′R,3′S,4′S,5′R)-6-chloro-4′-(3-chloro-2-fluoro-phenyl)-2′-(2,2-dimethyl-propyl)-2-oxo-1,2-dihydro-spiro[indole-3,3′-pyrrolidine]-5′-carboxylic acid (4-carbamoyl-phenyl)-amide, chiral 4-{[(2′R,3′S,4′S,5′R)-6-chloro-4′-(3-chloro-2-fluoro-phenyl)-2′-(2,2-dimethyl-propyl)-2-oxo-1,2-dihydro-spiro[indole-3,3′-pyrrolidin]e-5′-carbonyl]-amino}-3-methoxy-benzoic acid, chiral (2′R,3′S,4′S,5′R)-6-chloro-4′-(3-chloro-2-fluoro-phenyl)-2′-(2,2-dimethyl-propyl)-2-oxo-1,2-dihydro-spiro[indole-3,3′-pyrrolidine]-5′-carboxylic acid [4-(2-hydroxy-ethoxy)-2-methoxy-phenyl]-amide and chiral (2′R,3′S,4′S,5′R)-6-Chloro-4′-(3-chloro-2-fluoro-phenyl)-2′-(2,2-dimethyl-propyl)-2-oxo-1,2-dihydro-spiro[indole-3,3′-pyrrolidine]-5′-carboxylic acid (4-carbamoyl-2-methoxy-phenyl)-amide.

5. A pharmaceutical formulation comprising a compound of the formula

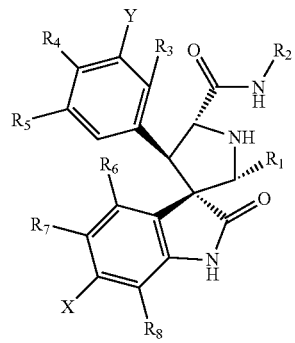

wherein
X is selected from the group consisting of F, Cl, and Br;
Y is selected from the group consisting of F, Cl, and Br;

$R_1$ is a substituted lower alkyl selected from

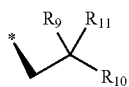

where $R_9$, $R_{10}$ are both methyl, or linked to form a cyclopropyl, cyclobutyl, cyclopentyl or cyclohexyl group;
$R_{11}$ is $(CH_2)_q$—$R_{12}$;
$R_{12}$ is selected from hydrogen, hydroxyl, lower alkyl, lower alkoxy, lower cycloalkenyl, substituted cycloalkenyl, lower cycloalkyl, substituted cycloalkyl, aryl, substituted aryl, hetereoaryl, substituted heteroaryl, hetereocycle or substituted heterocycle;
q is 0, 1 or 2;
$R_2$ is selected from the group consisting of aryl, substituted aryl, heteroaryl and substituted heteroaryl;
$R_3$, $R_4$, $R_5$ is selected from H or F with the proviso that at least two of $R_3$, $R_4$, $R_5$ are hydrogen;
$R_6$, $R_7$, $R_8$ is selected from H or F with the proviso that at least two of $R_6$, $R_7$, $R_8$ are hydrogen
and the pharmaceutically acceptable salts and enantiomers thereof together with a pharmaceutically acceptable excipient or carrier.

\* \* \* \* \*